US012698279B2

(12) United States Patent
Von Mentzer et al.

(10) Patent No.: US 12,698,279 B2
(45) Date of Patent: Aug. 4, 2026

(54) POLYMORPHS OF A HYDROCHLORIDE SALT OF PN6047

(71) Applicant: Pharmnovo AB, Lund (SE)

(72) Inventors: Bengt Von Mentzer, Kungshamn (SE); Ingemar Starke, Gothenburg (SE); Hans G. Nilsson, Värmdö (SE)

(73) Assignee: PHARMNOVO AB, Lund (SE)

( * ) Notice: Subject to any disclaimer, the term of this patent is extended or adjusted under 35 U.S.C. 154(b) by 827 days.

(21) Appl. No.: 18/015,828

(22) PCT Filed: Jul. 12, 2021

(86) PCT No.: PCT/EP2021/069340
§ 371 (c)(1),
(2) Date: Jan. 12, 2023

(87) PCT Pub. No.: WO2022/013153
PCT Pub. Date: Jan. 20, 2022

(65) Prior Publication Data

US 2023/0174525 A1 Jun. 8, 2023

(30) Foreign Application Priority Data

Jul. 17, 2020 (SE) .................................... 2050910-5

(51) Int. Cl.
*C07D 471/06* (2006.01)
*A61P 29/00* (2006.01)
*C07D 417/06* (2006.01)

(52) U.S. Cl.
CPC ............ *C07D 417/06* (2013.01); *A61P 29/00* (2018.01); *C07B 2200/13* (2013.01)

(58) Field of Classification Search
CPC .... C07D 417/06; C07B 2200/13; A61P 29/00
(Continued)

(56) References Cited

FOREIGN PATENT DOCUMENTS

| | | |
|---|---|---|
| CN | 02819582.5 | 11/2005 |
| CN | 107531670 | 12/2015 |

(Continued)

OTHER PUBLICATIONS

Berge ,Pharmaceutical Salts, Journal of Pharmaceutical Sciences, Jan. 1977, vol. 66 No. I, p. 1-19 (Year: 1977).*

(Continued)

*Primary Examiner* — Taylor V Oh
(74) *Attorney, Agent, or Firm* — Jeffrey S. Melcher; Melcher Patent Law PLLC

(57) ABSTRACT

The present invention relates to a hydrochloride salt of 4-[(3-carbamoylphenyl)[1-(1,3-thiazol-5-ylmethyl)piperidin-4-ylidene]methyl]-N,N-dimethylbenzamide (PN6047) and crystalline forms thereof, more specifically Form HCl2 and Form HCl3 of PN6047. The invention also relates to pharmaceutical compositions comprising such polymorphs, to a process for the preparation of these polymorphs, and to the use of these polymorphs in the treatment or prevention of conditions that are mediated by agonism of the δ-opioid receptor, and in particular in the treatment or prevention of pain.

(Continued)

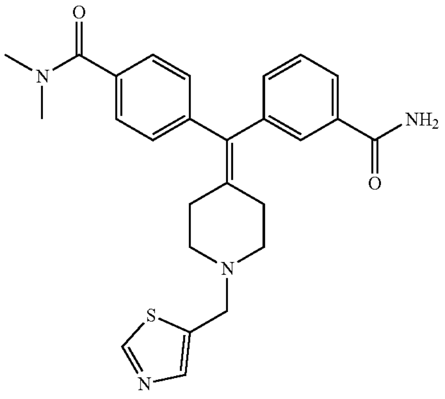

19 Claims, 9 Drawing Sheets

(58) Field of Classification Search
USPC .......................................................... 514/326
See application file for complete search history.

(56) References Cited

FOREIGN PATENT DOCUMENTS

| | | |
|---|---|---|
| JP | 2018501314 | 1/2018 |
| WO | 2003/029215 | 4/2003 |
| WO | 2016/099393 | 6/2016 |

OTHER PUBLICATIONS

Chinese Office Action issued in counterpart Chinese patent application No. 5106327, May 7, 2025, and translation, pp. 1-8.
International Search Report Issued in PCT/EP2021/069340, Sep. 17, 2021, pp. 1-2.
Written Opinion Issued in PCT/EP2021/069340, Sep. 17, 2021, pp. 1-5.
Hilfiker R (Editor) Ed—Hilfiker R: 11 Polymorphism in the Pharmaceutical Industry11, Jan. 1, 2006 (Jan. 1, 2006), Jan. 1, 2006, pp. 1-19, XP002528052, ISBN: 978-3-527-31146-0.
Kazuhide Ashizawa, Polymorphic Phenomena in Pharmaceuticals and the Science of Crystallisation, Maruzen Planet Co., Ltd, 2002, pp. 56-102 and 304-317.
Office Action issued in corresponding Japanese Patent Application No. 2023-503146, pp. 1-4, with translation.

* cited by examiner

POLYMORPHS OF A HYDROCHLORIDE SALT OF PN6047

CROSS-REFERENCE TO RELATED APPLICATIONS

This application claims priority to Swedish patent application No. 2050910-5 filed on Jul. 17, 2020, the contents of which is hereby incorporated by reference in its entirety.

TECHNICAL FIELD

The present invention relates to a hydrochloride salt of 4-[(3-carbamoylphenyl)[1-(1,3-thiazol-5-ylmethyl)piperidin-4-ylidene]methyl]-N,N-dimethylbenzamide (PN6047) and crystalline forms thereof, more specifically Form HCl2 and Form HCl3 of PN6047. The invention also relates to pharmaceutical compositions comprising such polymorphs, to a process for the preparation of these polymorphs, and to the use of these polymorphs in the treatment or prevention of conditions that are mediated by agonism of the 6-opioid receptor, and in particular in the treatment or prevention of pain.

BACKGROUND

The compound 4-[(3-carbamoylphenyl)[1-(1,3-thiazol-5-ylmethyl)piperidin-4-ylidene]methyl]-N,N-dimethylbenzamide (PN6047; structure shown below) is disclosed in WO 2016/099393. It is a highly potent 6-opioid receptor agonist, which retains analgesic potency on repeated administration. In contrast to existing analgesics, which only deliver moderate pain relief, PN6047 has the potential to produce maintained analgesia in pain states with less risk of unwanted side effects such as respiratory depression and constipation.

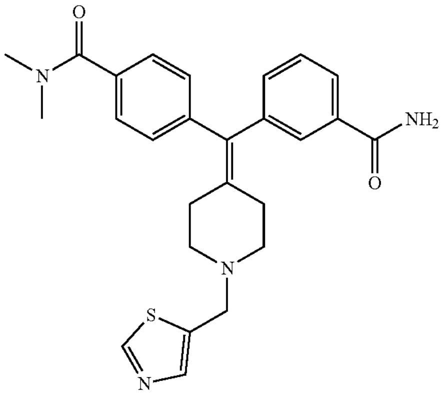 [SMILES: CN(C)C(=O)c1ccc(C(=C2CCN(Cc3cncs3)CC2)c2cccc(C(N)=O)c2)cc1]

For use in pharmaceutical preparations, it is desirable that the active pharmaceutical ingredient (API) is in a highly crystalline form. Non-crystalline (i.e., amorphous) materials may contain higher levels of residual solvents, which is undesirable. Also, because of their lower chemical and physical stability, as compared with crystalline material, amorphous materials may display faster decomposition and may spontaneously form crystals with a variable degree of crystallinity. This may result in unreproducible solubility rates and difficulties in storing and handling the material. Thus, there is a need for crystalline forms of PN6047 having improved properties with respect to stability, bulk handling and solubility. In particular, it is an object of the present invention to provide a stable crystalline form of PN6047 that exhibits a high solubility, contains low levels of residual solvents, has a high chemical stability and low hygroscopicity and can be obtained in high levels of crystallinity.

DETAILED DESCRIPTION OF THE INVENTION

It has been discovered that the hydrochloride (HCl) salt of PN6047 has certain advantages over the free base compound, including improved solubility in water at room temperature and an increase in bioavailability. It has further been discovered that the HCl salt of PN6047 may be present in different crystalline forms, or polymorphs. Some of these crystalline forms show good solubility, good chemical and physical stability (including solution stability) and low hygroscopicity and are therefore useful in pharmaceutical compositions of PN6047. In a first aspect, therefore, the invention relates to an HCl salt of PN6047. In some embodiments, the HCl salt is a crystalline salt.

In some embodiments, the invention provides a crystalline HCl salt of PN6047, which is stable at a relative humidity (RH) up to 60% at a temperature of 25° C. In some embodiments, the invention provides a crystalline HCl salt of PN6047, which is stable at a relative humidity up to 75% at a temperature of 40° C. Such crystalline HCl salts can be stable under these conditions for at least 1 day, 1 week, 1 month, 3 months, 6 months, 1 year, 2 years, 3 years or even longer.

Figure 1:
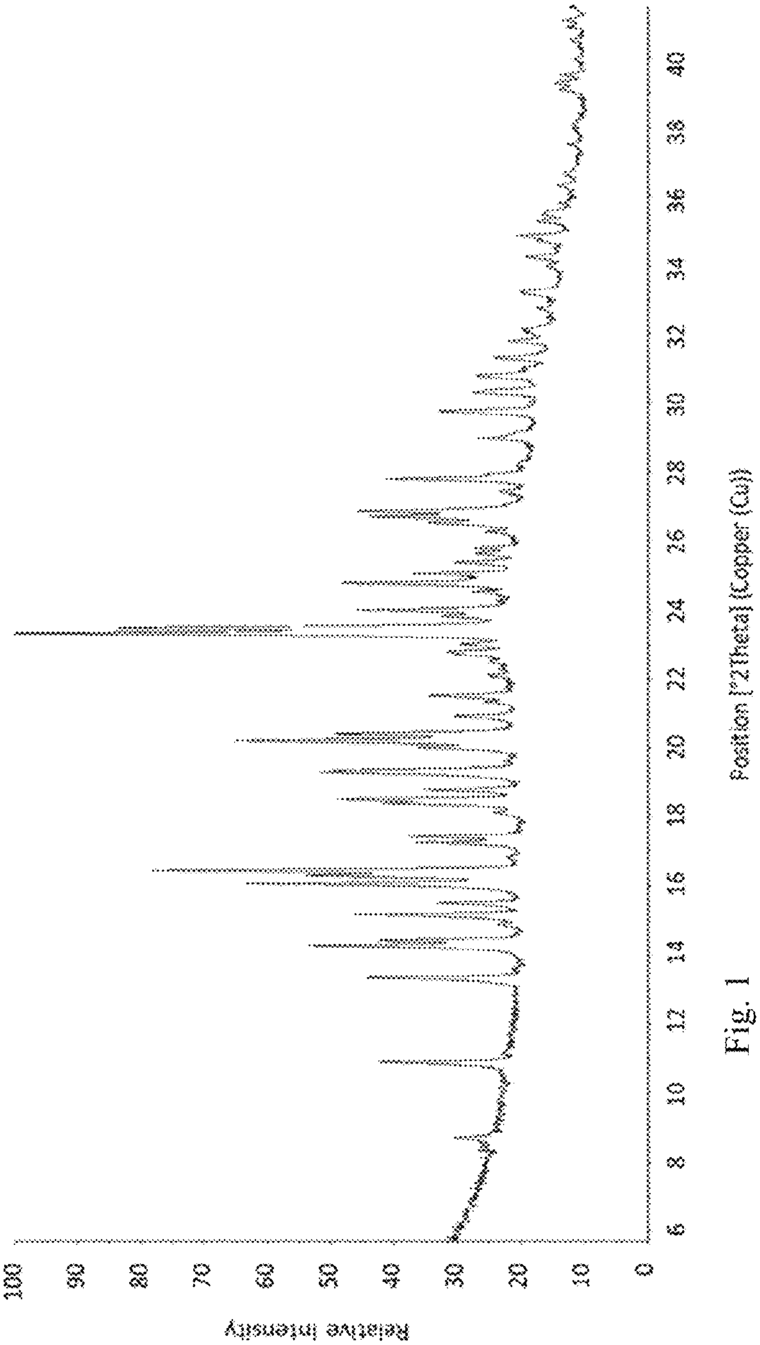
FIG. 1 shows the X-ray powder diffractogram of Form HCl2.

In one embodiment, the crystalline HCl salt of PN6047 is Form HCl2. This form may be prepared by crystallization from certain organic solvents, such as 2-propanol, acetone, acetonitrile, ethanol, ethyl acetate or tetrahydrofuran. In one embodiment, Form HCl2 has an X-ray powder diffraction (XRPD) pattern, obtained with CuKα1-radiation, with at least peaks at ° 2θ values of 16.5±0.2, 23.3±0.2 and 23.5±0.2. In some embodiments, Form HCl2 has an XRPD pattern, obtained with CuKα1-radiation, with at least peaks at ° 2θ values of 16.5±0.2, 23.3±0.2 and 23.5±0.2 and one or more of 14.3±0.2, 16.1±0.2, 16.3±0.2 and 20.2±0.2. In some embodiments, Form HCl2 has an XRPD pattern, obtained with CuKα1-radiation, with at least peaks at ° 2θ values of 14.3±0.2, 16.1±0.2, 16.3±0.2, 16.5±0.2, 20.2±0.2, 23.3±0.2 and 23.5±0.2. In some embodiments, Form HCl2 has an XRPD pattern, obtained with CuKα1-radiation, with at least peaks at ° 2θ values of 14.3±0.2, 16.1±0.2, 16.3±0.2, 16.5±0.2, 20.2±0.2, 23.3±0.2 and 23.5±0.2 and one or more of 15.2±0.2, 18.5±0.2, 19.4±0.2, 20.4±0.2, 24.0±0.2, 24.8±0.2 and 26.9±0.2. In some embodiments, Form HCl2 has an XRPD pattern, obtained with CuKα1-radiation, with at least peaks at ° 2θ values of 14.3±0.2, 15.2±0.2, 16.1±0.2, 16.3±0.2, 16.5±0.2, 18.5±0.2, 19.4±0.2, 20.2±0.2, 20.4±0.2, 23.3±0.2, 23.5±0.2, 24.0±0.2, 24.8±0.2 and 26.9±0.2. In a particular embodiment, the invention relates to Form HCl2, having an XRPD pattern, obtained with CuKα1-radiation, substantially as shown in FIG. 1.

Figure 2:
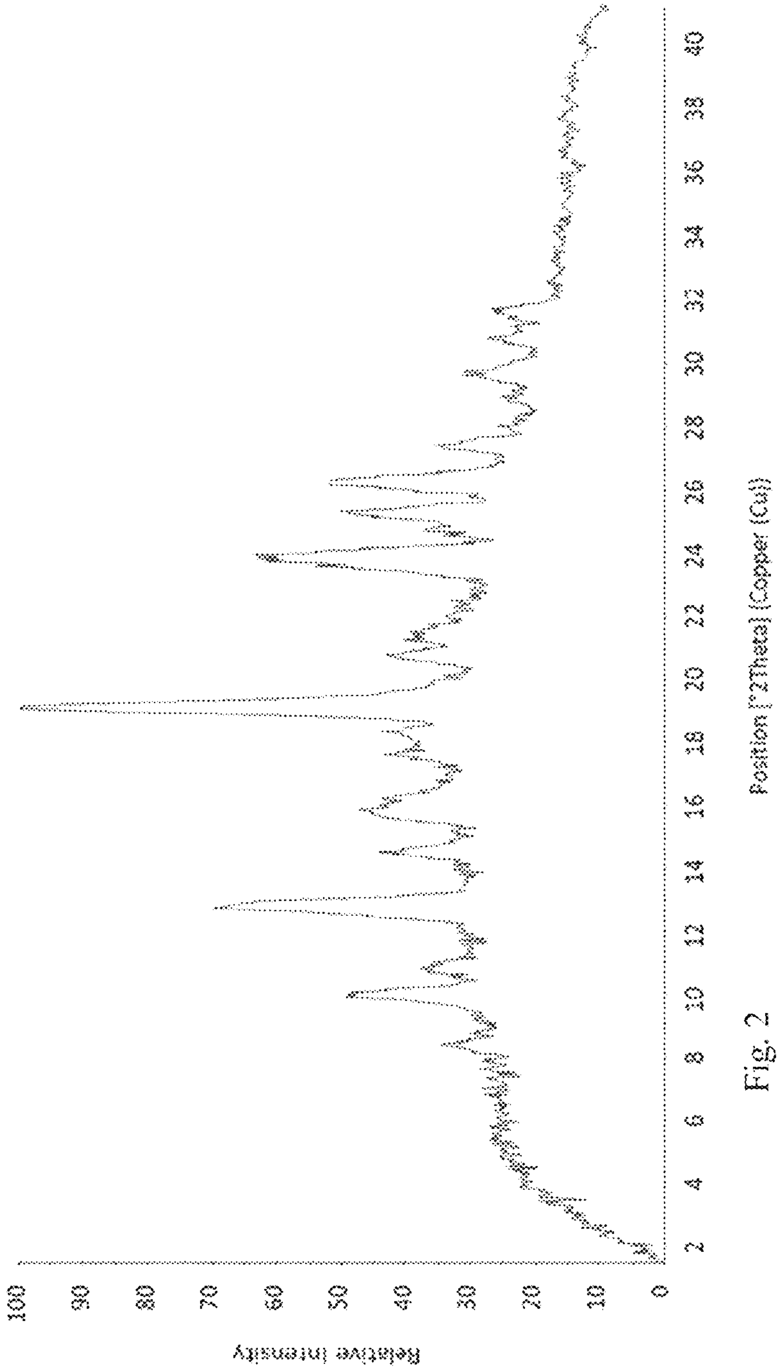
FIG. 2 shows the X-ray powder diffractogram of Form HCl3.

In another embodiment, the crystalline HCl salt of PN6047 is Form HCl3. This form may be isolated by evaporation of water from an aqueous solution, by crystallization from acetonitrile or by subjecting the amorphous HCl salt of PN6047 to 40° C./75% RH. It is believed that Form HCl3 is a hydrate. In one embodiment, Form HCl3 has an XRPD pattern, obtained with CuKα-radiation, with at least peaks at ° 2θ values of 12.8±0.2, 19.1±0.2 and 23.9±0.2. In some embodiments, Form HCl3 has an XRPD pattern, obtained with CuKα-radiation, with at least peaks at ° 2θ values of 12.8±0.2, 19.1±0.2 and 23.9±0.2 and one or more of 10.0±0.2, 25.3±0.2 and 26.3±0.2. In some embodiments, Form HCl3 has an XRPD pattern, obtained with CuKα-radiation, with at least peaks at ° 2θ values of 10.0±0.2, 12.8±0.2, 19.1±0.2, 23.9±0.2, 25.3±0.2 and 26.3±0.2. In some embodiments, Form HCl3 has an XRPD pattern, obtained with CuKα-radiation, with at least peaks at ° 2θ values 10.0±0.2, 12.8±0.2, 19.1±0.2, 23.9±0.2, 25.3±0.2 and 26.3±0.2, and one or more of 14.5±0.2, 16.2±0.2, 18.3±0.2, 20.8±0.2, 27.4±0.2 and 29.7±0.2. In some embodiments, Form HCl3 has an XRPD pattern, obtained with CuKα-radiation, with at least peaks at ° 2θ values of 10.0±0.2, 12.8±0.2, 14.5±0.2, 16.2±0.2, 18.3±0.2, 19.1±0.2, 20.8±0.2, 23.9±0.2, 25.3±0.2 and 26.3±0.2, 27.4±0.2 and 29.7±0.2. In a particular embodiment, the invention relates to Form HCl3, having an XRPD pattern, obtained with CuKα-radiation, substantially as shown in FIG. 2.

Form HCl2 may be a hydrate or an anhydrate. With a water uptake of approximately 2.2% at 25° C./80% RH, it shows moderate hygroscopicity. This moderate hygroscopicity is considered advantageous, as the water content of the crystals remains fairly constant even with humidity changes within the normal relative humidity range of about 30% to about 70% RH. It was observed that at higher relative humidity (e.g., >85% RH), Form HCl2 absorbs water and transforms into Form HCl3, which is believed to be a hydrate. This transformation is not reversible: drying of Form HCl3 did not result in Form HCl2 but in a less crystalline phase of Form HCl3. Nevertheless, it is believed that Form HCl2 is stable at conditions up to 85% RH. Stability studies showed that Form HCl2 is chemically stable in saline for up to 1 week, and is physically stable for at least up to 4 weeks at 25° C./60% RH, 40° C./75% RH and 60° C./38% RH.

It has been found that the solubility of the two crystalline HCl salts of PN6047 is considerably higher than that of the free base. For instance, whereas the free base only sparingly dissolves in water at pH 7 (<1 mg/mL), Forms HCl2 and HCl3 are highly soluble in water at the same pH (>100 mg/mL). The higher solubility of the HCl salt allows continued investigation of the compound at higher concentrations, which is advantageous e.g. in toxicology studies. Unexpectedly, it has also been discovered that the HCl salts of PN6047 have a significantly larger bioavailability than the free base. Specifically, the maximum bioavailability for Form HCl2 of PN6047 (as tested in rat) was 35% (oral 50 mg/kg), whereas the maximum bioavailability for the free base was only 8% (oral 3 mg/kg). It is expected that the increased bioavailability (and thus the increased exposure) of the HCl salt may lead to an improved efficacy of PN6047 in the treatment of pain and other indications as mentioned herein. Possibly, the increased bioavailability may allow the HCl salt to be administered in substantially lower doses than the free base. The unexpected increase in bioavailability of the HCl salt may also enable the use of sustained release formulations of the compound.

In another aspect, the invention relates to a pharmaceutical composition comprising a therapeutically effective amount of a crystalline HCl salt of PN6047 as disclosed herein, in association with one or more pharmaceutically acceptable excipients. The excipients may e.g. include fillers, binders, disintegrants, glidants and lubricants. In some embodiments, the crystalline HCl salt of PN6047 is Form HCl2. In some embodiments, the crystalline HCl salt of PN6047 is Form HCl3.

In some embodiments, the pharmaceutical composition comprises Form HCl2 or Form HCl3 having a polymorphic purity of at least about 90%. In some embodiments, the polymorphic purity is at least about 95%. In some embodiments, the polymorphic purity is at least about 98%. For example, the polymorphic purity is at least about 98.5%, such as at least about 99%, such as at least about 99.5%, such as at least about 99.8%, or such as at least about 99.9%. In some embodiments, the pharmaceutical composition comprises Form HCl2 and is substantially free of other crystalline HCl salts of PN6047. For example, in some embodiments, the pharmaceutical composition comprising Form HCl2 is substantially free of Form HCl3 of PN6047. In some embodiments, Form HCl2 contains less than about 15% by weight of Form HCl3 or any other crystalline HCl salt of PN6047. For example, Form HCl2 contains less than about 14%, about 13%, about 12%, about 11%, about 10%, about 9%, about 8%, about 7%, about 6%, about 5%, about 4%, about 3%, about 2%, about 1% or less by weight of Form HCl3 or any other crystalline HCl salt of PN6047.

In some embodiments, the pharmaceutical composition comprises Form HCl3 and is substantially free of other crystalline HCl salts of PN6047. For example, in some embodiments, the pharmaceutical composition comprising Form HCl3 is substantially free of Form HCl2 of PN6047. In some embodiments, Form HCl3 contains less than about 15% by weight of Form HCl2 or any other crystalline HCl salt of PN6047. For example, Form HCl3 contains less than about 14%, about 13%, about 12%, about 11%, about 10%, about 9%, about 8%, about 7%, about 6%, about 5%, about 4%, about 3%, about 2%, about 1% or less by weight of Form HCl2 or any other crystalline HCl salt of PN6047.

In some embodiments, the pharmaceutical composition comprises between about 0.5 and about 99.5% by weight of a crystalline HCl salt of PN6047 as disclosed herein. For example, the composition may comprise between about 0.5% and about 20%, between about 20% and about 40%, between about 40% and about 60%, between about 60% and about 80%, or between about 80% and 99.5% by weight of a crystalline HCl salt of PN6047 as disclosed herein. In some embodiments, the composition comprises about 5%, about 10%, about 15%, about 20%, about 25%, about 30%, about 35%, about 40%, about 45%, about 50%, about 55%, about 60%, about 65%, about 70%, about 77%, about 80%, about 85%, about 90% or about 95% by weight of a crystalline HCl salt of PN6047 as disclosed herein.

In some embodiments, the pharmaceutical composition comprises a filler. Examples of suitable fillers include, but are not limited to, dicalcium phosphate dihydrate, calcium sulfate, lactose (e.g. lactose monohydrate), sucrose, mannitol, sorbitol, cellulose, microcrystalline cellulose, dry starch, hydrolyzed starches and pregelatinized starch.

In some embodiments, the pharmaceutical composition comprises a binder. Examples of suitable binders include, but are not limited to, starch, pregelatinized starch, gelatin, sugars (such as sucrose, glucose, dextrose, lactose and sorbitol), polyethylene glycol, waxes, natural and synthetic gums (such as acacia gum and tragacanth gum), sodium alginate, cellulose derivatives (such as hydroxypropylmethylcellulose (or hypromellose), hydroxypropylcellulose and ethylcellulose) and synthetic polymers (such as acrylic acid and methacrylic acid copolymers, methacrylic acid copolymers, methyl methacrylate copolymers, aminoalkyl methacrylate copolymers, polyacrylic acid/polymethacrylic acid copolymers and polyvinylpyrrolidone (povidone)).

In some embodiments, the pharmaceutical composition comprises a disintegrant. Examples of suitable disintegrants include, but are not limited to, dry starch, modified starch (such as (partially) pregelatinized starch, sodium starch glycolate and sodium carboxymethyl starch), alginic acid, cellulose derivatives (such as sodium carboxymethylcellulose, hydroxypropyl cellulose, and low substituted hydroxypropyl cellulose (L-HPC)) and cross-linked polymers (such as carmellose, croscarmellose sodium, carmellose calcium and cross-linked PVP (crospovidone)).

In some embodiments, the pharmaceutical composition comprises a glidant or lubricant. Examples of suitable glidants and lubricants include, but are not limited to, talc, magnesium stearate, calcium stearate, sodium stearyl fumarate, stearic acid, glyceryl behenate, colloidal anhydrous silica, aqueous silicon dioxide, synthetic magnesium silicate, fine granulated silicon oxide, starch, sodium lauryl sulfate, boric acid, magnesium oxide, waxes (such as carnauba wax), hydrogenated oil, polyethylene glycol, sodium benzoate, polyethylene glycol, and mineral oil.

In general, pharmaceutical compositions may be prepared in a conventional manner using conventional excipients. In some embodiments, the ingredients of the composition are mixed to a homogenous mixture and then formulated as tablets or capsules. The homogenous mixture of the ingredients may be compressed into tablets using conventional techniques, such as rotary tablet press. Alternatively, the mixture may be wetted by the addition of a liquid, such as water and/or an appropriate organic solvent (e.g., ethanol or isopropanol), and thereafter granulated and dried. The granules obtained may then be compressed into tablets using conventional techniques. Tablets may be coated with one or more coating layers. The coating layers may comprise e.g. polysaccharides (such as a sugar or a starch), cellulose-based polymers, polyvinyl-based polymers, acrylate copolymers, or mixtures thereof. The one or more coating layers may provide a modified release of the active ingredient, such as delayed release, extended release, slow release, controlled release or sustained release of the active ingredient.

Capsules (such as hard gelatine capsules) may comprise a powder mixture or small multiparticulates (such as granules, extruded pellets or minitablets) of the ingredients, or a liquid or semisolid formulation of the ingredients. For soft gelatine capsules, the crystalline HCl salt of PN6047 may be admixed with, for example, a vegetable oil or polyethylene glycol.

Formulations for use in nasal administration or oral inhalation (e.g., nebulized solutions) may comprise an aqueous solution of a crystalline HCl salt of PN6047 together with, for example, a suitable preservative such as benzalkonium chloride. Formulations for use in topical administration (e.g. an ointment or a cream) may comprise a crystalline HCl salt of PN6047 in admixture with, for example, an oil or a wax and a suitable preservative.

In another aspect, the invention relates to the crystalline HCl salts of PN6047 disclosed herein for use in therapy. The crystalline HCl salts of PN6047 disclosed herein are useful in the treatment or prevention of pain, including, but not limited to, acute pain, chronic pain, neuropathic pain, cancer pain, visceral pain, diabetic pain, and pain caused by diseases or conditions such as rheumatoid arthritis, osteoarthritis, fibromyalgia, migraine and opioid-induced hyperalgesia (OIH). They may also be used as an analgesic agent, e.g. during general anesthesia and monitored anesthesia care.

The crystalline HCl salts of PN6047 disclosed herein are further useful in the treatment or prevention of various mental disorders, such as depression, anxiety, and substance use disorders (including alcohol, nicotine, opioid and other drug abuse or addiction). They are further useful in the treatment of withdrawal and abstinence syndromes resulting from the chronic use of opioids and other drugs which produce a negative affective state including hypersensitivity to emotional and painful stimuli. Other diseases and conditions that can be treated or prevented with the crystalline HCl salts of PN6047 disclosed herein comprise neurodegenerative disorders (including stroke, Alzheimer's Disease, Parkinson's Disease), cardiovascular disease (including ischemic heart disease), epilepsy, urinary incontinence, sensory hypersensitivity (including chronic cough and itch), lung edema, various gastro-intestinal disorders (including irritable bowel syndrome and irritable bowel disease), spinal injury, disorders of the sympathetic nervous system (such as hypertension).

The crystalline HCl salts of PN6047 disclosed herein may also be used as immunomodulators, especially for autoimmune diseases, such as rheumatoid arthritis and osteoarthritis, for skin grafts and for organ transplants. They are also useful in disease states where degeneration or dysfunction of opioid receptors is present or implicated.

Thus, in one embodiment, the invention relates to the crystalline HCl salts of PN6047, as disclosed herein, for use in the treatment or prevention of a disease or condition as listed above.

In another embodiment, the invention relates to the use of the crystalline HCl salts of PN6047, as disclosed herein, in the manufacture of a medicament for the treatment or prevention of a disease or condition as listed above.

In yet another embodiment, the invention relates to a method for treatment or prevention of a disease or condition as listed above in a warm-blooded animal, comprising administering a therapeutically effective amount of a crystalline HCl salt of PN6047 as disclosed herein, to a warm-blooded animal in need of such treatment or prevention.

In some embodiments, a crystalline HCl salt of PN6047 as disclosed herein may be administered in combination with at least one other therapeutically active agent, such as with one, two, three or more other therapeutically active agents. The crystalline HCl salt of PN6047 and the at least one other therapeutically active agent may be administered simultaneously, sequentially or separately. Therapeutically active agents that are suitable for combination with a crystalline HCl salt of PN6047 include, but are not limited to, known active agents that are useful in the treatment of any of the aforementioned conditions, disorders and diseases.

In one embodiment, a crystalline HCl salt of PN6047 as disclosed herein is administered in combination with one or more other analgesic agents. Combinations of different analgesic agents (with different properties) are often used to achieve a balance of effects necessary for maintaining an anesthetic state (e.g. amnesia, analgesia, muscle relaxation and sedation). The one or more other analgesic agents may e.g. be an anesthetic agent, a hypnotic agent, an anxiolytic agent, a neuromuscular blocker, a neuropeptide receptor blocker or an opioid. Specific examples of such compounds include, but are not limited to, tricyclic antidepressants, gabapentinoids, CGRP receptor antagonists, benzodiazepines and ketamine.

In another embodiment, a crystalline HCl salt of PN6047 as disclosed herein is administered in combination with one or more other compounds that are useful in the treatment or prevention of pain. Examples of such compounds include, but are not limited to, opioid receptor agonists and antagonists, cannabinoids, alpha-2 adrenoceptor agonists, purinoceptor antagonists, transient receptor potential channel blockers, sodium channel blockers, calcium channel blockers, and potassium channel blockers.

In another aspect, the invention relates to a process for the preparation of Forms HCl2 and HCl3 of PN6047. In some embodiments, Form HCl2 can be formed by direct crystallization from an appropriate solvent. In some embodiments, the solvent is 2-propanol, acetone, acetonitrile, ethanol, ethyl acetate or tetrahydrofuran. In a preferred embodiment, the solvent is 2-propanol. In some embodiments, Form HCl3 can be formed by direct crystallization from an appropriate solvent, or by evaporation of solvent from a solution. In some embodiments, the solvent is water or acetonitrile.

In some embodiments, the process for the preparation of Form HCl2 of PN6047 comprises the steps of:

a) preparing a solution or a suspension of a HCl salt of PN6047 in a suitable solvent;
b) maintaining stirring until a solid is obtained, or until conversion into Form HCl2 is completed;
c) recovering the solid obtained in step b); and
d) drying the solid under vacuum.

Form HCl2 of PN6047 may also be obtained when the free base is used as the starting material. In some embodiments, therefore the process for the preparation of Form HCl2 of PN6047 comprises the steps of:

a) preparing a solution or a suspension of the free base of PN6047 in a suitable solvent;
b) adding a HCl solution to the solution or suspension of step a) to achieve a free base:HCl ratio of about 1:1;
c) maintaining stirring until a solid is obtained, or until conversion into Form HCl2 is completed;
d) recovering the solid obtained in step c); and
e) drying the solid under vacuum.

The free base of PN6047 used in step a) may be crystalline or amorphous.

As used herein, the term “polymorph” refers to crystals of the same molecule that have different physical properties as a result of the order of the molecules in the crystal lattice. Polymorphs of a single compound have one or more different chemical, physical, mechanical, electrical, thermodynamic, and/or biological properties from each other. Differences in physical properties exhibited by polymorphs can affect pharmaceutical parameters such as storage stability, compressibility, density (important in composition and product manufacturing), dissolution rates (an important factor in determining bioavailability), solubility, melting point, chemical stability, physical stability, powder flowability, water sorption, compaction, and particle morphology. Differences in stability can result from changes in chemical reactivity (e.g. differential oxidation, such that a dosage form discolours more rapidly when comprised of one polymorph than when comprised of another polymorph) or mechanical changes (e.g., crystal changes on storage as a kinetically favoured polymorph converts to a thermodynamically more stable polymorph) or both (e.g., one polymorph is more hygroscopic than the other). As a result of solubility/dissolution differences, some transitions affect potency and/or toxicity. In addition, the physical properties of the crystal may be important in processing; for example, one polymorph might be more likely to form solvates or might be difficult to filter and wash free of impurities (i.e., particle shape and size distribution might be different between one polymorph relative to the other). “Polymorph” does not include amorphous forms of the compound.

As used herein, the term “amorphous” refers to a non-crystalline form of a compound which may be a solid state form of the compound or a solubilized form of the compound. For example, “amorphous” refers to a compound without a regularly repeating arrangement of molecules or external face planes.

As used herein, the term “anhydrate” or “anhydrous form” refers to a polymorph (i.e., crystalline HCl salt) of PN6047 that has 1% or less by weight water, for example 0.5% or less, 0.25% or less, or 0.1% or less by weight water.

As used herein, the term “hydrate” refers to a polymorph of PN6047 wherein the crystal lattice comprises crystal water.

The term “non-stoichiometric hydrate” refers to a polymorph of PN6047 that comprises water but wherein variations in the water content do not cause significant changes to the crystal structure. In some embodiments, a non-stoichiometric hydrate can refer to a crystalline HCl salt of a PN6047 that has channels or networks throughout the crystal structure into which water molecules can diffuse. During drying of non-stoichiometric hydrates, a considerable proportion of water can be removed without significantly disturbing the crystal network, and the crystals can subsequently rehydrate to give the initial non-stoichiometric hydrated crystalline form. Unlike stoichiometric hydrates, the dehydration and rehydration of non-stoichiometric hydrates is not accompanied by a phase transition, and thus all hydration states of a non-stoichiometric hydrate represent the same crystal form. In some embodiments, a non-stoichiometric hydrate can have up to about 20% by weight water, such as about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, about 2%, or about 1% water by weight. In some embodiments, a non-stoichiometric hydrate can have between 1% and about 20% by weight water, such as between about 1% and about 5%, about 1% and about 10%, about 1% and about 15%, about 2% and about 5%, about 2% and about 10%, about 2% and about 15%, about 2% and about 20%, about 5% and about 10%, about 5%) and about 15%, about 5% and about 20%, about 10% and about 15%, about 10% and about 20%, or about 15% and about 20% by weight water.

In some embodiments the % water by weight in a crystal form, such as a non-stoichiometric hydrate, is determined by the Karl Fischer titration method. In some embodiments, the crystal form is dried prior to Karl Fischer titration.

As used herein, the term “polymorphic purity” when used in reference to a composition comprising a polymorph of PN6047, refers to the percentage of one specific polymorph relative to another polymorph or an amorphous form of PN6047 in the referenced composition. For example, a composition comprising Form HCl2 having a polymorphic purity of 90% would comprise 90 weight parts Form HCl2 and 10 weight parts of other crystalline and/or amorphous forms of PN6047.

As used herein, the terms "effective amount" or "therapeutically effective amount" refer to a sufficient amount of a crystalline HCl salt of PN6047 that, following administration to a subject, will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic use is the amount of PN6047 required to provide a clinically significant decrease in disease symptoms. An appropriate "effective" amount in any individual case is determined using any suitable technique, such as a dose escalation study.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

As used herein, the term "pharmaceutically acceptable" refers to those compounds, materials, compositions and/or dosage forms that are suitable for human pharmaceutical use and that are generally safe, non-toxic and neither biologically nor otherwise undesirable.

As used herein, a compound or composition is "substantially free" of one or more other components if the compound or composition contains no significant amount of such other components. Such components can include starting materials, residual solvents, or any other impurities that can result from the preparation of and/or isolation of the compounds and compositions provided herein. In some embodiments, a polymorph form provided herein is substantially free of other polymorph forms. In some embodiments, a particular polymorph (i.e., crystalline HCl salt) of PN6047 is "substantially free" of other polymorphs if the particular polymorph constitutes at least about 95% by weight of PN6047 present. In some embodiments, a particular polymorph of PN6047 is "substantially free" of other polymorphs if the particular polymorph constitutes at least about 97%, about 98%, about 99%, or about 99.5% by weight of PN6047 present.

As used herein, a compound is "substantially present" as a given polymorph if at least about 50% by weight of the compound is in the form of that polymorph, for example if at least about 60%, at least about 70%, at least about 80%, or at least about 90% by weight of the compound is in the form of that polymorph. In some embodiments, at least about 95%, such as at least about 96%, such as at least about 97%, such as at least about 98%, such as at least about 99% or such as at least about 99.5% by weight of the compound is in the form of that polymorph.

As used herein, the term "stable" means that the polymorphs do not exhibit a change in one or more of polymorph form (e.g., an increase or decrease of a certain form), appearance, pH, percent impurities, activity (as measured by in vitro assays), or osmolarity over time. In some embodiments, the polymorphs provided herein are stable for at least 1, 2, 3 or 4 weeks. For example, the polymorphs do not exhibit a change in one or more of polymorph form (e.g., an increase or decrease of a certain form), appearance, pH, percent impurities, activity (as measured by in vitro assays), or osmolarity over at least 1, 2, 3 or 4 weeks. In some embodiments, the polymorphs provided herein are stable for at least 1, 2, 3, 4, 5, 6, 7, 8, 9, 10, 11 or 12 months. For example, the polymorphs do not exhibit a change in one or more of polymorph form (e.g., an increase or decrease of a certain form), appearance, pH, percent impurities, activity (as measured by in vitro assays), or osmolarity over at least 1, 2, 3, 4, 5, 6, 7, 8, 9, 10, 11 or 12 months. In the above, the phrase "do not exhibit a change" refers to a change of less than 5% (e.g., less than 4%, less than 3%, less than 2%, less than 1%) as measured for any of the parameters over the relevant time period.

The crystallinity of a polymorph of PN6047 may be measured e.g. by X-Ray Powder Diffraction (XRPD) methods or by Differential Scanning Calorimetry (DSC) methods. When reference is made herein to a crystalline compound, preferably the crystallinity is greater than about 70%, such as greater than about 80%, particularly greater than about 90%, more particularly greater than about 95%. In some embodiments, the degree of crystallinity is greater than about 98%. In some embodiments, the degree of crystallinity is greater than about 99%. The % crystallinity refers to the percentage by weight of the total sample mass which is crystalline.

As used herein, the term "about" refers to a value or parameter herein that includes (and describes) embodiments that are directed to that value or parameter per se. For example, description referring to "about 20" includes description of "20." Numeric ranges are inclusive of the numbers defining the range. Generally speaking, the term "about" refers to the indicated value of the variable and to all values of the variable that are within the experimental error of the indicated value (e.g., within the 95% confidence interval for the mean) or within 10 percent of the indicated value, whichever is greater.

The invention will now be described by the following examples which do not limit the invention in any respect. All cited documents and references mentioned herein are incorporated by reference in their entireties.

Abbreviations h hour(s)
min minute(s)
TFE 2,2,2-trifluoroethanol
THF tetrahydrofuran
rpm revelations per minute

Experimental Methods

The amorphous HCl salt of PN6047 was prepared by lyophilization of a mixture of the free base of PN6047 and an HCl aqueous solution. 500.5 mg of free base was dissolved in 5 mL TFE/water 1:1 (v/v). To this solution was added 1.2 mL of a 1M aqueous HCl solution to achieve a free base:HCl ratio of 1:1. The solution was liquid-dozed into 11 HPLC vials, frozen in liquid nitrogen and placed under deep vacuum using a freeze dryer (Alpha 2-4 LD, Christ). After lyophilization, HT-XRPD confirmed that the material was amorphous. The material was then dried under deep vacuum (1 mbar) at 80° C. for 3 days to remove any residual solvent. $^{1}$H NMR analysis confirmed the formation of the HCl salt after lyophilization and the chemical integrity of PN6047.

X-Ray Powder Diffraction (XRPD) Analysis

High Throughput X-ray powder diffraction (HT-XRPD) patterns were obtained using the Crystallics T2 high-throughput XRPD set-up. The plates were mounted on a Bruker General Area Detector Diffraction System (GADDS) equipped with a VANTEC-500 gas area detector corrected for intensity and geometric variations. The calibration of the measurement accuracy (peaks position) was performed using NIST SRM1976 standard (Corundum). Data collection was carried out at room temperature using monochromatic Cu Kα radiation in the 2θ region between 1.50 and 41.5°. The diffraction pattern of each well was collected in two 2θ ranges (1.5°≤2θ≤21.5° for the first frame, and 19.5°≤2θ≤41.5° for the second) with an exposure time of 45 seconds for each frame. No background subtraction or curve smoothing was applied to the XRPD patterns.

High Resolution X-ray powder diffraction (HR-XRPD) data were collected on a D8 Advance diffractometer using Cu Kα1 radiation (1.54056 Å) with a germanium monochromator at room temperature. Diffraction data were collected in the 2θ range 1.5-41.5 ° 2θ. Detector scan on solid state LynxEye detector was performed using 0.0160 per step with 4 second/step scan speed. The samples were measured in an 8 mm long glass capillary with 0.4 mm outer diameter.

It is known in the art that an X-ray powder diffraction pattern may be obtained having one or more measurement errors depending on measurement conditions (such as equipment, sample preparation or machine used). In particular, it is generally known that intensities in an XRPD pattern may fluctuate depending on measurement conditions and sample preparation. For example, persons skilled in the art of XRPD will realize that the relative intensities of peaks may vary according to the orientation of the sample under the test and on the type and setting of the instrument used. The skilled person will also realize that the position of reflections can be affected by the precise height at which the sample sits in the diffractometer and the zero calibration of the diffractometer. The surface planarity of the sample may also have a small effect. Hence a person skilled in the art will appreciate that the diffraction pattern presented herein is not to be construed as absolute and any crystalline form that provides a powder diffraction pattern substantially identical to those disclosed herein fall within the scope of the present disclosure (for further information, see R. Jenkins and R. L. Snyder, "Introduction to X-ray powder diffractometry", John Wiley & Sons, 1996).

Thermogravimetric Analysis (TGA)

Analyses were performed on a TGA/DSC 3+ STARe system (Mettler Toledo GmbH, Switzerland). The TGA/DSC 3+ was calibrated for temperature with indium and aluminum. Samples (circa 2 mg) were weighed into 100 μL aluminum crucibles and sealed. The seals were pin-holed and the crucibles heated in the TGA from 25 to 300° C. at a heating rate of 10° C./min unless stated otherwise. Dry $N_2$ gas was used for purging.

Differential Scanning Calorimetry (DSC)

Analyses were performed on a heat flux DSC3+ STARe system (Mettler-Toledo GmbH, Switzerland). The DSC3+ was calibrated for temperature and enthalpy with a small piece of indium (m.p.=156.6° C.; δHf=28.45 J/g) and zinc (m.p.=419.6° C.; δHf=107.5 J/g). Samples (circa 2 mg) were sealed in standard 40 μL aluminum pans, pin-holed and heated in the DSC from 25° C. to 300° C., at a heating rate of 10° C./min unless stated otherwise. Dry $N_2$ gas at a flow rate of 50 mL/min was used to purge the DSC equipment during measurement.

Dynamic Vapour Sorption (DVS)

Analyses were performed on a DVS-1 system from Surface Measurement Systems (London, UK). Weight equilibration per step was set at dm/dt<0.002 for a minimum of 1 hour or a maximum of 6 hours. The sample was subjected to a sorption-desorption-sorption cycle running from 40 to 95 to 0 to 45% RH, at a constant temperature of 25° C. One cycle consisted of 20 steps, those between 0 and 90% RH were taken in 10% RH each. Afterwards the sample was measured by HT-XRPD.

EXAMPLES

Example 1

Preparation of Forms HCl2 and HCl3

Slurries of amorphous HCl salt of PN6047 were prepared in neat solvents, as shown in Table 1 below. About 45 mg of amorphous salt was mixed with a solvent at room temperature. The mixtures were then placed in a Crystal16™ apparatus and subjected to the temperature profile as displayed in FIG. 3. After the temperature profile, the solids were separated from the liquids by centrifugation. The solid phases were dried at ambient conditions and under deep vacuum (5 mbar) and analyzed by HT-XRPD before and after exposure to accelerated aging conditions (AAC; 3 days at 40° C./75% RH). The liquid phases were also dried under deep vacuum (5 mbar) and the recovered solids were analyzed by HT-XRPD.

TABLE 1

Experimental conditions for the thermocycling experiments

| Solvent | Solvent volume [μL] | Dissolved at initial temp. | Solids after temp. profile | Ambient | Vacuum | Ambient (AAC) | Vacuum (AAC) |
|---|---|---|---|---|---|---|---|
| 2-propanol | 300 | no | yes | HCl2 | HCl2 | HCl2 | HCl2 |
| acetone | 400 | no | yes | HCl2 | HCl2 | HCl2 | HCl2 |
| acetonitrile | 300 | no | yes | HCl2 | HCl2 | HCl2 | HCl2 |
| ethanol | 100 | yes | yes | HCl2 | HCl2 | HCl2 | HCl2 |
| ethyl acetate | 200 | no | yes | HCl2 | HCl2 | HCl2 | HCl2 |
| THF | 200 | no | yes | HCl2 | HCl2 | HCl2 | HCl2 |
| water* | 50 | yes | no | HCl3 | HCl3 | HCl3 | HCl3 |

*Recovered from the liquid phase

The XRPD peaks for Form HCl2 are listed in Table 2 below. The HR-diffractogram for Form HCl2 is shown in FIG. 2.

TABLE 2

XRPD peaks of Form HCl2

| Position [° 2θ] | d-spacing [Å] | Rel. Int. [%] |
|---|---|---|
| 8.72 | 10.14 | 8 |
| 10.90 | 8.11 | 26 |
| 13.34 | 6.63 | 31 |
| 14.28 | 6.20 | 42 |
| 14.43 | 6.13 | 28 |
| 15.17 | 5.84 | 33 |
| 15.52 | 5.70 | 16 |
| 16.08 | 5.51 | 54 |
| 16.31 | 5.43 | 42 |
| 16.46 | 5.38 | 73 |
| 17.27 | 5.13 | 21 |
| 17.44 | 5.08 | 22 |
| 18.41 | 4.82 | 27 |
| 18.51 | 4.79 | 36 |

TABLE 2-continued

| XRPD peaks of Form HCl2 | | |
|---|---|---|
| Position [° 2θ] | d-spacing [Å] | Rel. Int. [%] |
| 18.80 | 4.72 | 19 |
| 19.35 | 4.58 | 35 |
| 20.03 | 4.43 | 20 |
| 20.23 | 4.39 | 57 |
| 20.42 | 4.34 | 36 |
| 20.94 | 4.24 | 13 |
| 21.53 | 4.12 | 18 |
| 22.81 | 3.90 | 14 |
| 23.02 | 3.86 | 12 |
| 23.34 | 3.81 | 100 |
| 23.51 | 3.78 | 80 |
| 23.83 | 3.73 | 15 |
| 24.01 | 3.70 | 33 |
| 24.78 | 3.59 | 36 |
| 25.04 | 3.55 | 22 |
| 25.39 | 3.51 | 14 |
| 26.53 | 3.36 | 19 |
| 26.71 | 3.33 | 31 |
| 26.86 | 3.32 | 34 |
| 27.81 | 3.21 | 29 |
| 29.75 | 3.00 | 20 |
| 30.33 | 2.95 | 13 |
| 30.79 | 2.90 | 13 |

Figure 3:
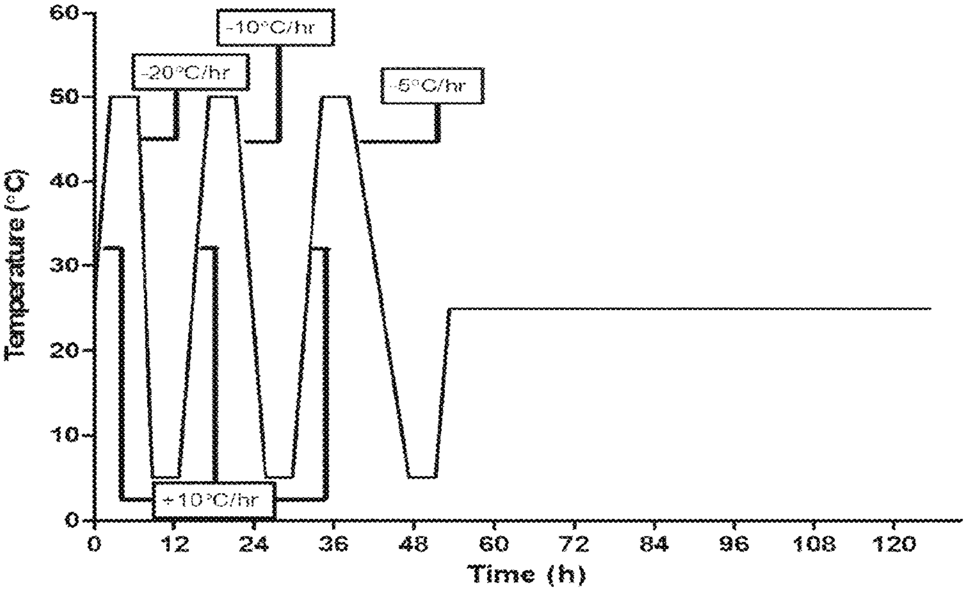
FIG. 3 shows the temperature profile of the thermocycling experiments.

The XRPD peaks for Form HCl3 are listed in Table 3 below. The HT-diffractogram for Form HCl3 is shown in FIG. 3.

TABLE 3

| XRPD peaks of Form HCl3 | | |
|---|---|---|
| Position [° 2θ] | d-spacing [Å] | Rel. Int. [%] |
| 8.39 | 10.52 | 15 |
| 9.98 | 8.86 | 33 |
| 10.80 | 8.19 | 14 |
| 12.81 | 6.91 | 55 |
| 14.50 | 6.10 | 19 |
| 15.77 | 5.61 | 22 |
| 16.19 | 5.47 | 17 |
| 17.65 | 5.02 | 16 |
| 18.34 | 4.83 | 17 |
| 19.11 | 4.64 | 100 |
| 20.76 | 4.27 | 18 |
| 21.40 | 4.15 | 13 |
| 23.86 | 3.73 | 52 |
| 24.74 | 3.60 | 15 |
| 25.27 | 3.52 | 33 |
| 26.27 | 3.39 | 39 |
| 27.40 | 3.25 | 18 |
| 28.95 | 3.08 | 8 |
| 29.71 | 3.00 | 17 |
| 30.78 | 2.90 | 13 |
| 31.72 | 2.82 | 13 |

Example 2

Differential Scanning Calorimetry (DSC) Analysis

Figure 4:
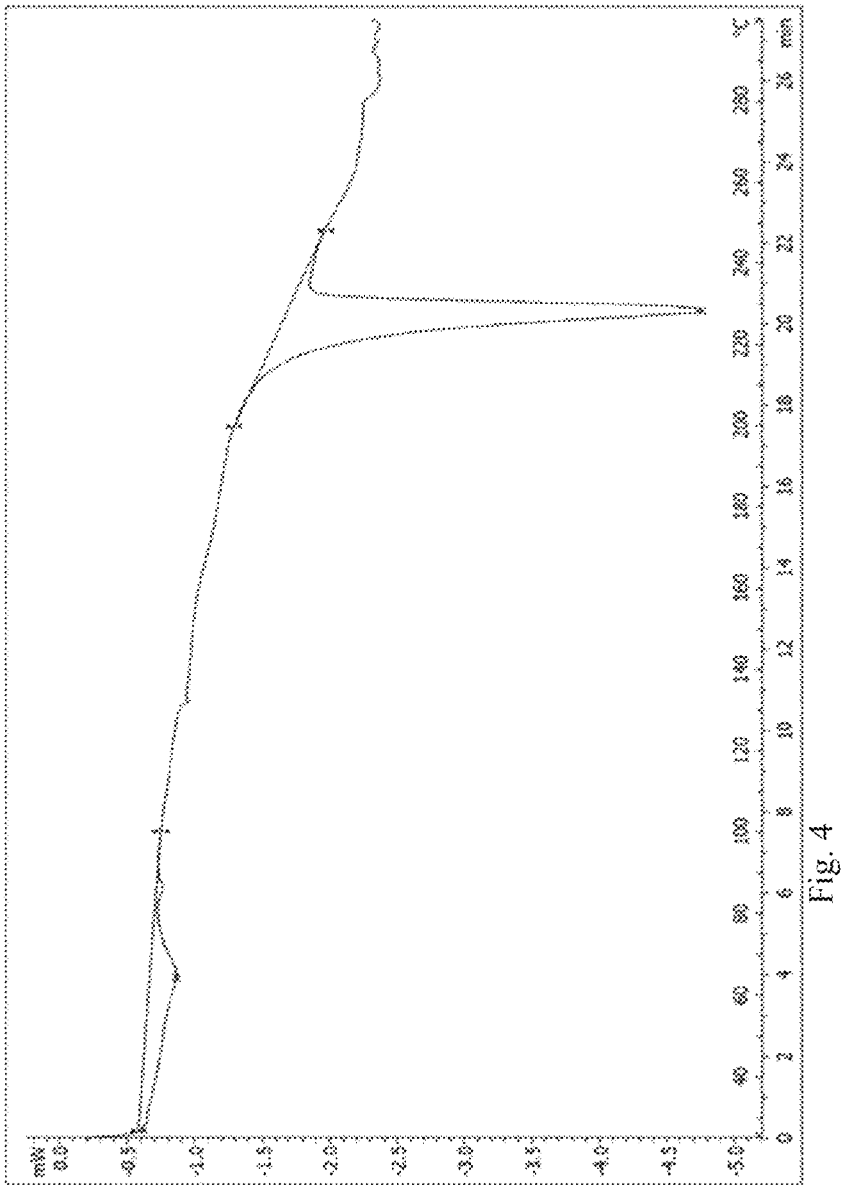
FIG. 4 shows the differential scanning calorimetry (DSC) thermogram of Form HCl2.

Form HCl2 displayed a broad endothermic event between about 25 and about 100° C. due to the loss of water. Thereafter, an endothermic event was observed at approximately 228° C. (onset 222.0° C.; endset 231.5° C.; peak 227.9° C.), which may be attributed to the melting of an anhydrous HCl salt. The DSC thermogram is shown in FIG. 4.

Figure 5:
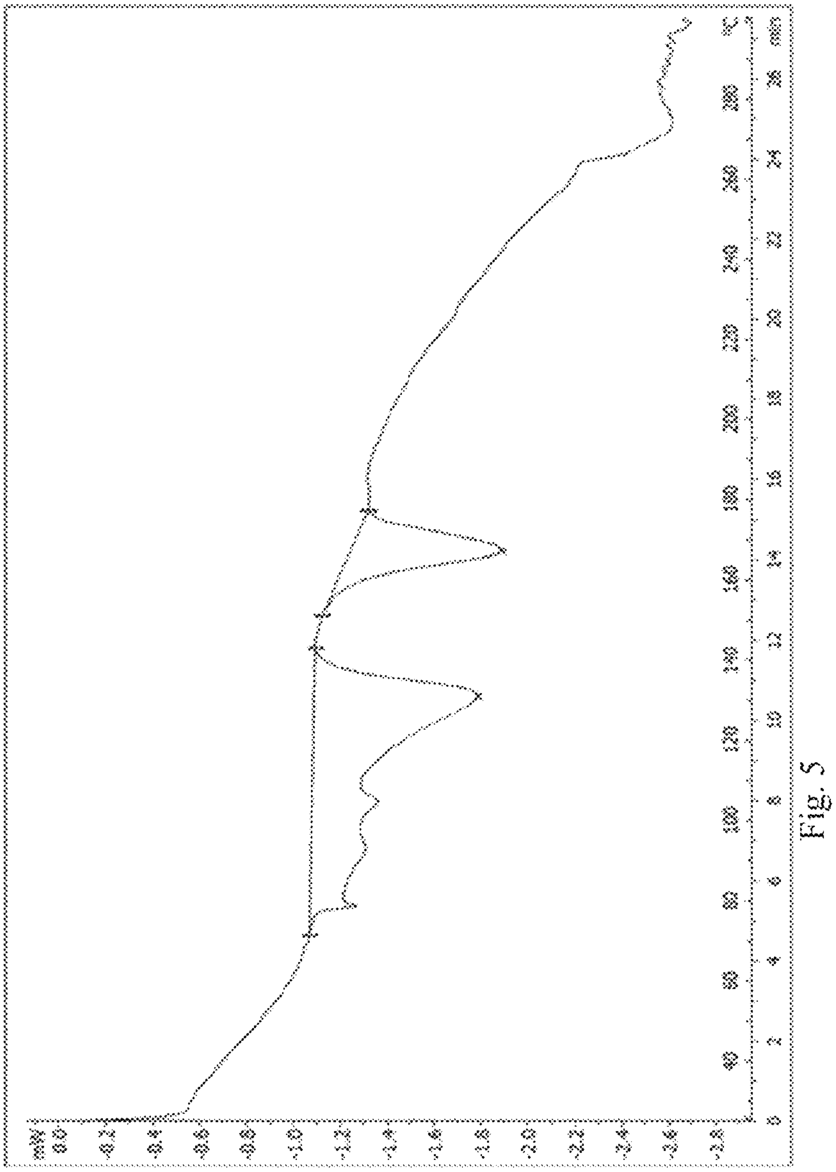
FIG. 5 shows the DSC thermogram of Form HCl3.

Form HCl3 shows a broad endothermic event between about 70 and about 150° C. due to the loss of water, which could be attributed to the dehydration of form HCl3. An endothermic event was then observed at approximately 167° C. (onset 159.8° C.; endset 175.2° C.; peak 166.9° C.), which may be attributed to the melting of an anhydrous HCl salt. The DSC thermogram is shown in FIG. 5.

Example 3

Thermogravimetric Analysis

Figure 6:
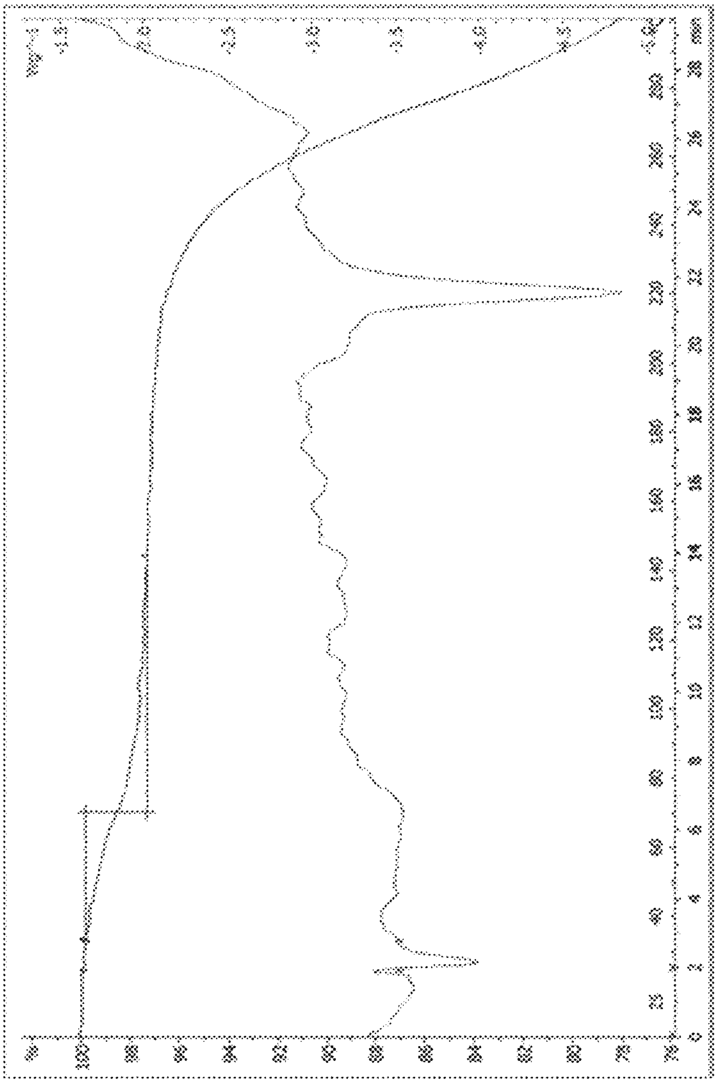
FIG. 6 shows the thermogravimetric analysis (TGA) and the heatflow thermograms of Form HCl2.

The sample of Form HCl2 showed a mass loss of 2.5% in the range of about 30 to about 160° C. This mass loss can most likely be attributed to the removal of water. Thermal decomposition of the sample started at about 220° C. The TGA and the heatflow thermograms are shown in FIG. 6.

Figure 7:
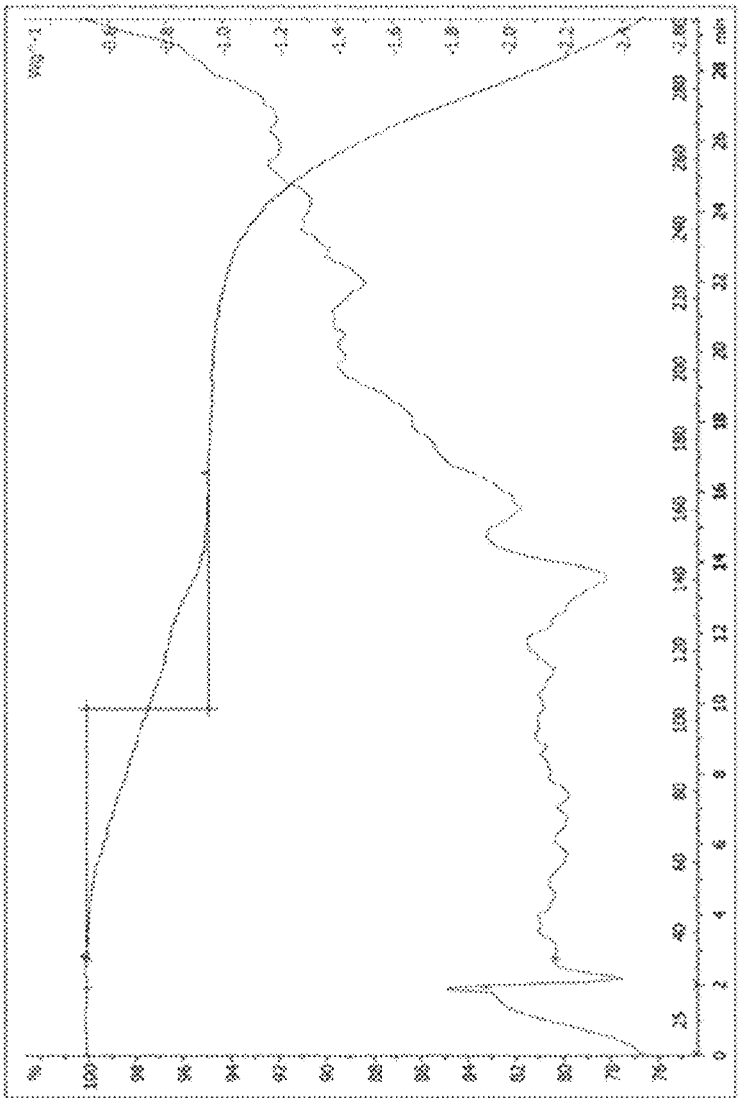
FIG. 7 shows the TGA and the heatflow thermograms of Form HCl3.

The sample of Form HCl3 showed a mass loss of 5.1% in the range of about 30 to about 160° C. This mass loss was attributed to the removal of water. Thermal decomposition of the sample started at about 220° C. The TGA and the heatflow thermograms are shown in FIG. 7.

Example 4

Dynamic Vapour Sorption (DVS) Analysis

Figure 8:
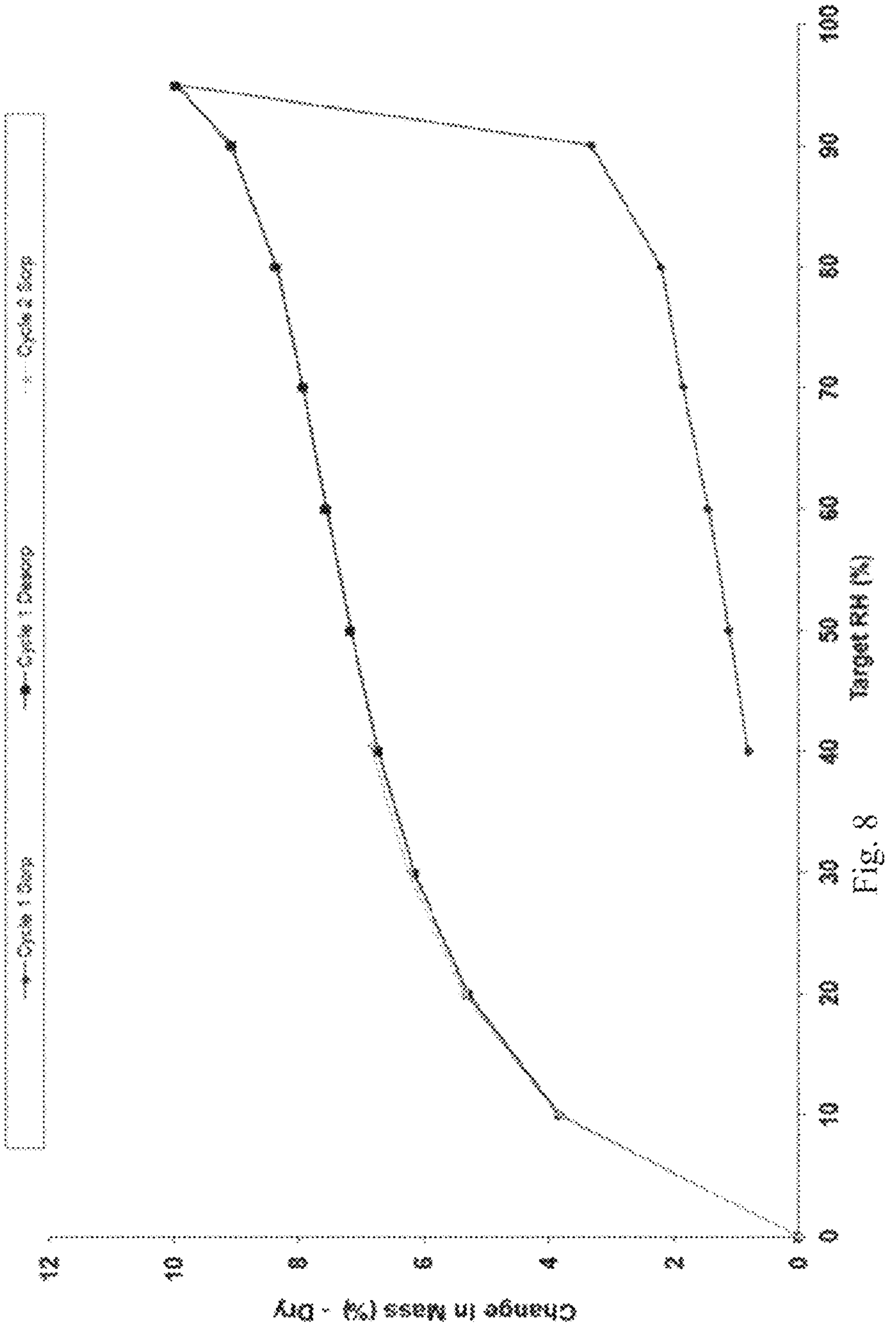
FIG. 8 shows the dynamic vapour sorption (DVS) isotherm plot of Form HCl2.

Forms HCl2 and HCl3 were subjected to DVS measurements to determine the hygroscopicity of these two forms. The DVS isotherm plot for form HCl2 is shown in FIG. 8. The material initially took up water slowly with increasing relative humidity (RH) up to about 90% RH. The change in mass was approximately 3.3%, corresponding to about 1 molecule of water per molecule of PN6047. At 25° C./80% RH, the water uptake was approximately 2.2%, which (according to the hygroscopicity classification as per the European Pharmacopoeia) makes the material moderately hygroscopic. From 90 to 95% RH, the mass of the material increased significantly from 3.3 to 10.0%, corresponding to about 2 additional molecules of water per molecule of PN6047. The material was then gradually dried from 95 to 0% RH in steps of 10% RH. The corresponding mass change upon drying was different than the initial mass increase upon hydration. Finally, from 0 to 40% RH, the water uptake proceeded in the same way as in the preceding dehydration step. After the DVS cycle, the material was analyzed by HT-XRPD, which showed that conversion had taken place from form HCl2 to form HCl3. It is believed that the uptake of the 2 additional molecules of water may have led to a change from form HCl2 to form HCl3.

Figure 9:
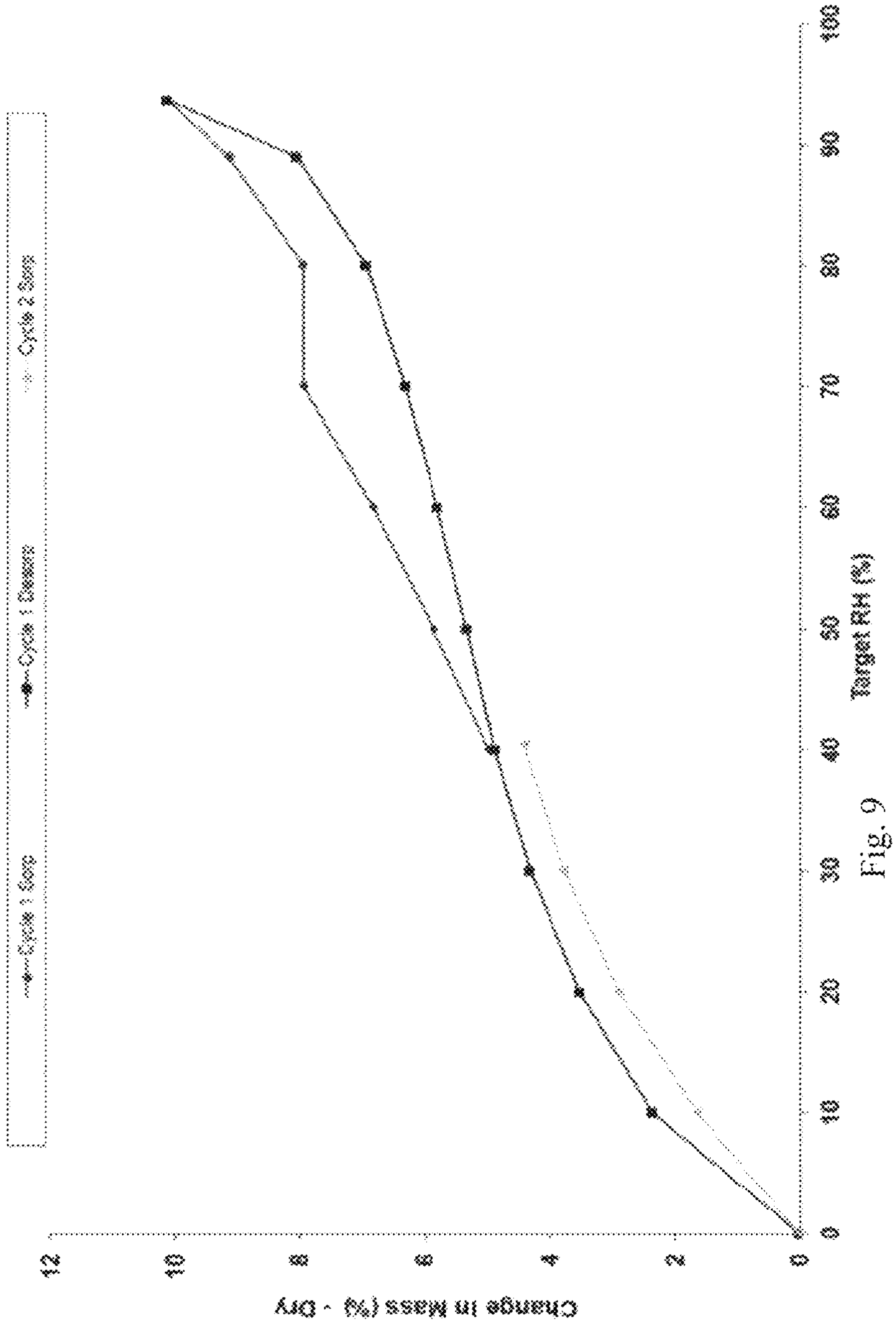
FIG. 9 shows the DVS isotherm plot of Form HCl3.

The DVS isotherm plot for form HCl3 is shown in FIG. 9. The material gradually took up water with increasing relative humidity (RH) up to 95% RH. At 25° C./80% RH, the water uptake was approximately 8.0%, which (according to the hygroscopicity classification as per the European Pharmacopoeia) makes the material moderately hygroscopic. The material was then gradually dried from 95 to 0% RH in steps of 10% RH. The corresponding mass change upon drying was approximately the same as the initial mass increase upon hydration. Finally, from 0 to 40% RH, the water uptake proceeded in the same way as the preceding dehydration step. After the DVS cycle, the material was analyzed by HT-XRPD which showed that form HCl3 was still present.

To further understand the hygroscopic nature of form HCl2, a sample of the material was incubated at 85% RH at room temperature for 2 days. The material was then analyzed by XRPD, which showed that conversion into form HCl3 had taken place.

A sample of Form HCl3 was further incubated at 50° C./1 mbar for 2 days to determine whether conversion to Form HCl2 would take place. However, the material was recovered as a poorly crystalline phase of Form HCl3, with additional diffraction peaks that could not be associated to any of the HCl forms.

Example 5

Larger Scale Preparation of Form HCl2

Form HCl2 was prepared from 2-propanol in scale-up experiments, as outlined in Table 4 below. In one experiment, 2-propanol was added to the amorphous HCl salt of PN6047. The suspension was stirred for 1 h at 50° C. In two other experiments, crystalline free base was suspended in 2-propanol and the suspensions were stirred at 1000 rpm using a magnetic stirring bar. To these suspensions was added a 37% HCl solution so as to achieve a free base:HCl ratio of 1:1. The suspensions were then stirred at elevated temperatures.

TABLE 4

Experimental conditions for scale-up experiments

| Entry | Free base [mg] | 37% HCl [μL] | 2-propanol [mL] | Conditions |
|---|---|---|---|---|
| 1 | 529 | 108 | 5.0 | 50° C., 1 h |
| 2 | 532 | 108 | 6.5 | 80° C., 18 h |
| 3 | 2162 | 440 | 21.0 | 50° C., 3 days |

After complete conversion into Form HCl2 was confirmed by HT-XRPD, the suspensions were subjected to centrifugation and the liquid phases were removed from the solid phases using a pipette. The solid phases were dried at 50° C. for 18 h and the resulting solids were analyzed by XRPD.

Example 6

Stability Studies of Form HCl2

Solution Stability Study

Experiments were performed in saline (0.9% NaCl in water). Two stock solutions of Form HCl2 in saline were prepared, one with a concentration of 10 mg/mL and one with a concentration of 100 mg/mL. The 10 mg/mL stock solution was prepared by dissolving 56 mg of material in 5 mL of saline. The 100 mg/mL stock solution was prepared by dissolving 196.2 mg of material in 1.75 mL saline. For each experiment involving 10 mg/mL, 0.5 mL of stock solution was transferred to an HPLC vial whereas for each experiment involving 100 mg/mL, 0.15 mL of stock solution was transferred to an HPLC vial. The HPLC vials were closed with a screw cap and placed in a Crystal16™ apparatus and incubated at different temperatures.

After the incubation time, the samples were diluted with acetonitrile/water 1:1 (v/v) and measured by LCMS to determine the API peak area. The experimental details and results are shown in Table 5.

TABLE 5

Experimental conditions for solution-stability experiments in saline

| HCl2 [mg] | Saline [mL] | Conc. [mg/mL] | Temp. [° C.] | Incubation time [d] | LCMS API [area %] |
|---|---|---|---|---|---|
| 5 | 0.5 | 10 | 25 | 0 | 99.9 |
| 15 | 0.15 | 100 | 25 | 0 | 99.9 |
| 5 | 0.5 | 10 | 5 | 3 | 99.9 |
| 15 | 0.15 | 100 | 5 | 3 | 99.9 |
| 5 | 0.5 | 10 | 25 | 3 | 99.9 |
| 15 | 0.15 | 100 | 25 | 3 | 99.9 |
| 5 | 0.5 | 10 | 40 | 3 | 99.9 |
| 15 | 0.15 | 100 | 40 | 3 | 99.9 |
| 5 | 0.5 | 10 | 5 | 4 | 99.9 |
| 15 | 0.15 | 100 | 5 | 4 | 99.9 |
| 5 | 0.5 | 10 | 25 | 4 | 99.9 |
| 15 | 0.15 | 100 | 25 | 4 | 99.9 |
| 5 | 0.5 | 10 | 40 | 4 | 99.9 |
| 15 | 0.15 | 100 | 40 | 4 | 99.9 |
| 5 | 0.5 | 10 | 5 | 7 | 99.9 |
| 15 | 0.15 | 100 | 5 | 7 | 99.9 |
| 5 | 0.5 | 10 | 25 | 7 | 99.9 |
| 15 | 0.15 | 100 | 25 | 7 | 99.9 |
| 5 | 0.5 | 10 | 40 | 7 | 99.9 |
| 15 | 0.15 | 100 | 40 | 7 | 100.0 |

Solid-State Stability Study

The solid-state stability of Form HCl2 was determined by incubating samples of approximately 18 mg at different conditions (temperature and relative humidity). After 1 week and 4 weeks, the samples were analyzed by XRPD to determine the polymorphic form, by TGA to determine the mass loss upon heating and by LCMS to determine the API purity. The experimental details and results are described in Table 6.

TABLE 6

Experimental conditions for solid-state stability experiments.

| HCl2 [mg] | Incubation Time | Conditions | XRPD | TGA mass loss [wt %] | LCMS API [area %] |
|---|---|---|---|---|---|
| — | 0 | — | HCl2 | 1.0 | 100 |
| 18.0 | 1 week | 25° C./ 60% RH | HCl2 | 1.8 | 100 |
| 19.4 | 1 week | 40° C./ 75% RH | HCl2 | 1.9 | 100 |
| 17.5 | 1 week | 60° C./ 38% RH | HCl2 | 1.9 | 100 |
| 17.6 | 4 weeks | 25° C./ 60% RH | HCl2 | 1.5 | 100 |
| 18.0 | 4 weeks | 40° C./ 75% RH | HCl2 | 1.6 | 100 |
| 19.3 | 4 weeks | 60° C./ 38% RH | HCl2 | 1.9 | 100 |

Example 7

Bioavailability Studies

Male Wistar rats were used. Six groups of four animals each were used. Two groups were administered a single intravenous dose of 1 mg/kg of the free base or the HCl2 salt, one group was administered a single oral dose of 3 mg/kg of the free base, and three groups were administered a single oral dose of 3, 10 or 50 mg/kg of the HCl2 salt. Blood samples were collected after 0.25, 0.5, 1, 2, 4, 6, 8 and 24 hours following intravenous administration, and after 0.083, 0.25, 0.5, 1, 2, 4, 6, 8 and 24 hours following oral administration. The samples were analyzed using an LC/MS/MS system. The bioavailability (Fabs) is shown in Table 7 and was calculated as follows:

$$\text{Fabs} = 100 \times \frac{AUCpo \times \text{Dose } iv}{AUCiv \times \text{Dose } po}$$

TABLE 7

Bioavailability.

| Form of PN6047 | Dose | Bioavailability (Fabs) |
|---|---|---|
| Free base | oral 3 mg/kg | 8% |
| HCl2 salt | oral 3 mg/kg | 24% |
| HCl2 salt | oral 10 mg/kg | 35.5% |
| HCl2 salt | oral 50 mg/kg | 34.6% |

The invention claimed is:

1. A crystalline HCl salt of PN6047 having a structure:

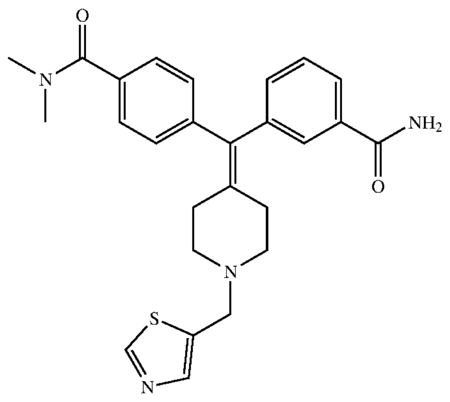 [SMILES: CN(C)C(=O)c1ccc(C(=C2CCN(Cc3cncs3)CC2)c2cccc(C(N)=O)c2)cc1]

which is Form HCl2 having an XRPD pattern, obtained with CuKaI-radiation, with at least peaks at °2θ values of 16.5±0.2, 23.3±0.2 and 23.5±0.2.

2. The crystalline HCl salt of claim 1, wherein the salt is stable at a relative humidity of 60% at a temperature of 25° C.

3. The crystalline HCl salt of claim 1, wherein the salt is stable at a relative humidity of 75% at a temperature of 40° C.

4. The crystalline HCl salt of claim 1, wherein the salt is an anhydrate.

5. The crystalline salt of claim 1, wherein Form HCl2 has an XRPD pattern, obtained with CuKα1-radiation, with at least peaks at °2θ values of 16.5±0.2, 23.3±0.2 and 23.5±0.2 and one or more of 14.3±0.2, 16.1±0.2, 16.3±0.2 and 20.2±0.2.

6. The crystalline salt of claim 1, wherein Form HCl2 has an XRPD pattern, obtained with CuKα1-radiation, substantially as shown in FIG. 1.

7. The crystalline HCl salt of claim 1, wherein Form HCl2 has a DSC curve comprising an endotherm at approximately 228° C.

8. A crystalline HCl salt of PN6047 having a structure:

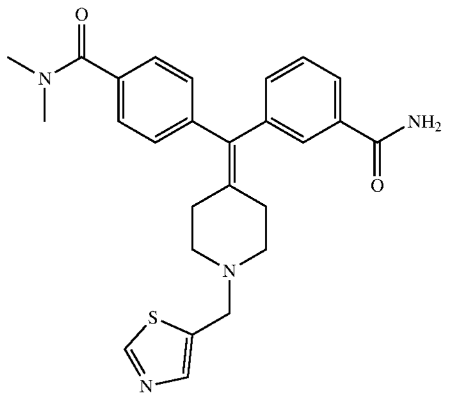 [SMILES: CN(C)C(=O)c1ccc(C(=C2CCN(Cc3cncs3)CC2)c2cccc(C(N)=O)c2)cc1]

which is Form HCl3, having an XRPD pattern, obtained with CuKα-radiation, with at least peaks at °2θ values of 12.8±0.2, 19.1±0.2 and 23.9±0.2.

9. The crystalline salt of claim 8, wherein Form HCl3 has an XRPD pattern, obtained with CuKα-radiation, with at least peaks at °2θ values of 12.8±0.2, 19.1±0.2 and 23.9±0.2 and one or more of 10.0±0.2, 25.3±0.2 and 26.3±0.2.

10. The crystalline salt of claim 8, wherein Form HCl3 has an XRPD pattern, obtained with CuKα-radiation, substantially as shown in FIG. 2.

11. The crystalline HCl salt of claim 8, wherein Form HCl3 has a DSC curve comprising an endotherm at approximately 167° C.

12. The crystalline HCl salt of claim 1, having a crystallinity of greater than about 99%.

13. A pharmaceutical composition comprising a therapeutically effective amount of a crystalline HCl salt of PN6047 according to claim 1, in association with one or more pharmaceutically acceptable excipients.

14. The pharmaceutical composition of claim 13, wherein the HCl salt of PN6047 is Form HCl2 having a polymorphic purity of at least about 90%.

15. The pharmaceutical composition of claim 14, wherein Form HCl2 is substantially free of Form HCl3.

16. A method of using crystalline HCl salt of PN6047 according to claim 1 in the treatment of pain comprising administering a therapeutically effective amount of the crystalline HCl salt of PN6047 to a patient.

17. A method of using crystalline HCl salt of PN6047 according to claim 16, wherein the pain is acute pain, chronic pain, neuropathic pain, cancer pain, visceral pain, diabetic pain, or pain caused by diseases or conditions including rheumatoid arthritis, osteoarthritis, fibromyalgia, migraine and opioid-induced hyperalgesia (OIH).

18. A process for the preparation of Form HCl2 of PN6047 having a structure:

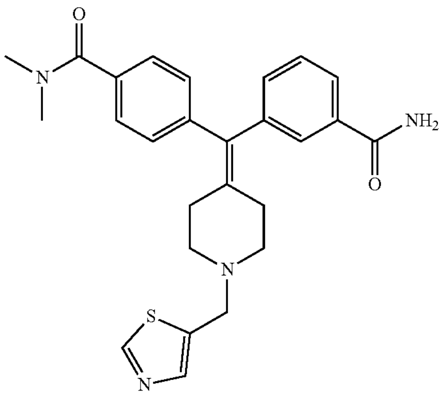 [SMILES: CN(C)C(=O)c1ccc(C(=C2CCN(Cc3cncs3)CC2)c2cccc(C(N)=O)c2)cc1]

having an XRPD pattern, obtained with CuKaI-radiation, with at least peaks at 20 values of 16.5±0.2, 23.3±0.2 and 23.5±0.2, comprising the steps of:

a) preparing a solution or a suspension of a HCl salt of PN6047 in a suitable solvent;

b) maintaining stirring until a solid is obtained, or until conversion into Form HCl2 is completed;

c) recovering the solid obtained in step b); and d) drying the solid under vacuum.

19. A process for the preparation of Form HCl2 of PN6047 having a structure:

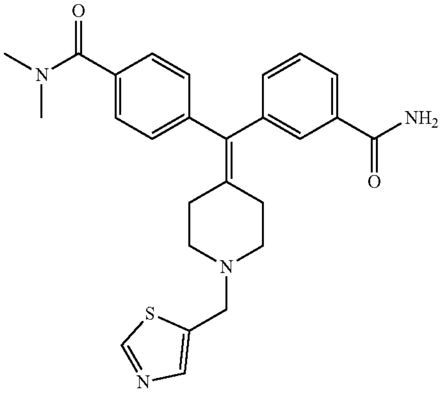 [SMILES: CN(C)C(=O)c1ccc(C(=C2CCN(Cc3cncs3)CC2)c2cccc(C(N)=O)c2)cc1]

having an XRPD pattern, obtained with CuKaI-radiation, with at least peaks at 20 values of 16.5±0.2, 23.3±0.2 and 23.5±0.2, comprising the steps of:

a) preparing a solution or a suspension of the free base of PN6047 in a suitable solvent;

b) adding a HCl solution to the solution or suspension of step a) to achieve a free base:HCl ratio of about 1:1;

c) maintaining stirring until a solid is obtained, or until conversion into Form HCl2 is completed;

d) recovering the solid obtained in step c); and e) drying the solid under vacuum.

* * * * *